(12) United States Patent
Schwan-Jonczyk et al.

(10) Patent No.: US 6,730,493 B1
(45) Date of Patent: May 4, 2004

(54) METHOD FOR DETERMINING THE STATE OF SUBSTANCES CONTAINING KERATIN AND SUITABLE DEVICES AND MEANS THEREFOR

(75) Inventors: Annette Schwan-Jonczyk, Darmstadt (DE); Lutz Haalck, Muenster (DE); Ceylan Uensal, Meerbusch (DE); Rainer Feldbruegge, Muenster (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/509,897

(22) PCT Filed: Aug. 3, 1999

(86) PCT No.: PCT/EP99/05568

§ 371 (c)(1),
(2), (4) Date: May 30, 2000

(87) PCT Pub. No.: WO00/08465

PCT Pub. Date: Feb. 17, 2000

(30) Foreign Application Priority Data

Aug. 4, 1998 (DE) .......................... 198 35 055

(51) Int. Cl.⁷ .......................... C12Q 1/37; C12Q 1/34; C12Q 1/00; G01N 21/00; G01N 21/75
(52) U.S. Cl. .............................. 435/23; 435/4; 435/18; 435/24; 436/164; 436/166
(58) Field of Search .............................. 435/23, 24, 18, 435/4; 436/164, 166

(56) References Cited

U.S. PATENT DOCUMENTS

| | | | |
|---|---|---|---|
| 4,430,488 A | | 7/1982 | Asakura |
| 4,665,741 A | | 5/1987 | Kabacoff |
| 5,247,345 A | * | 9/1993 | Curtis |
| 5,324,642 A | * | 6/1994 | Baumgartner |
| 5,443,961 A | | 8/1995 | L'Oreal |
| 5,461,925 A | | 10/1995 | Nguyen |
| 5,580,785 A | | 12/1996 | Stiffey |
| 5,844,686 A | * | 12/1998 | Treptow et al. |

FOREIGN PATENT DOCUMENTS

| | | |
|---|---|---|
| EP | 0 458 594 A | 11/1991 |
| EP | 0 458 644 A | 11/1991 |
| EP | 0 702 232 A | 3/1996 |

OTHER PUBLICATIONS

Hilterhaus–Bong et al. (1989). Contributions to the chemistry of human hair: III. Protein chemical aspects of permanent waving treatments. International Journal of Cosmetic Science, 11(5), pp 221–232.*
Friedrich, A.B. Und Antrasnikian, G., Appl. Environ. Microbiol. 62:2875, 1996.
Boeckle, B., Et Al, Appl. Environ. Microbio. 61:3705, 1995.
Gotoch, T. Et Al., Bioschi. Biotechnol. Biochem. 59–367, 1995.
Lin, X. Appl. Environ. Microbiol. 61 (4): 1469–1474, 1995.
Cheng, S.W., Biosci. Biotechnol. Biochem 59 (12): 2239–2243, 1995.
Kilpatric, D. J., Et A., Text. Res J. 40:25, 1970.
Bjorath, J., Et Al., Eur. J. Biochem. 176:441,1'988.
Robbins, C.R. & Bahl, M. J. Soc. Cosmet. Chem. 35:379, 1984.
Iwto 11062 (D), Neue Ausgabe 1966.
Iwto 4–60, Neue Ausgabe 1966.
Clark, H.T., J. Biol. Chem 97:235, 1932.

* cited by examiner

*Primary Examiner*—Ralph Gitomer
*Assistant Examiner*—Mahreen Chaudhry
(74) *Attorney, Agent, or Firm*—Michael J. Striker

(57) ABSTRACT

The method for recognizing damage and determining the extent of the damage to a keratin-containing material, such as hair or wool, includes subjecting a sample of it in aqueous solution to an enzymatic and/or chemical treatment for proteolytic or hydrolytic degradation of the sample, and subsequently measuring the turbidity of the resulting liquid sample to determine the extent of the damage, either by visual observation with the naked eye or by physical measurement methods. An apparatus suitable for performing the method and enzymes, such as proteases and proteinases, and chemical agents for carrying out the method are also described.

26 Claims, 8 Drawing Sheets

METHOD FOR DETERMINING THE STATE OF SUBSTANCES CONTAINING KERATIN AND SUITABLE DEVICES AND MEANS THEREFOR

BACKGROUND OF THE INVENTION

1. Field of the Invention

The present invention relates to a method for assessing and determining the condition of keratin-containing materials, particularly the condition of hair, with existing structural damage caused by external factors such as the environment, weathering, natural aging, physical or chemical noxae or cosmetic treatments, to agents and devices that are appropriate therefor and to the use thereof.

2. Related Art

Keratin-containing materials including the skin and skin appendages, for example hair, nails, feathers and hoofs, are subject to a multitude of natural and unnatural physical and chemical influences. These include energy-rich radiation (for example UV light), weather conditions or weathering (for example temperature, air humidity or air composition), cosmetic treatments, for example hair bleaching, permanent wave treatments, coloring or enameling. Such influences manifest themselves in varying degrees of structural modifications of these materials leading to a possible change in their chemical and physical properties. In the case of, for example, hair, this can result in a loss of gloss, suppleness, hold or combability. In addition, the brittleness and splitting of hair increases. The degree of damage increases with the frequency and duration of exposure to the influencing parameters.

For an effective use of hair-care, hair-conditioning or hair-restructuring agents it is necessary not only to recognize the current condition of the hair with reliability but, in particular, to make a correct selection of the agents for permanent waving, coloring and bleaching of hair that are adapted to a particular hair structure. This, however, requires a reliable determination of the degree of hair damage. The hair condition can be determined either visually or in tactile manner by subjective evaluation of, for example, gloss, brittleness, coarseness or the appearance of splitting, or this can be done by use of objective measuring methods.

The method of subjective assessment of hair condition or hair damage is fast and simple. The recognition of incipient and advanced structural changes (hair damage) based on subjective parameters, however, leads to highly erratic or unusable results either because of a lack of experience in assessing the hair condition or hair damage or else owing to masking of the damage by hair-care agents.

Numerous methods are known for objective examination of keratin-containing materials for the purpose of detecting any damage that may be present. An example is the determination of the cysteine content by high-pressure liquid chromatography (HPLC). This method has the drawback that it requires comprehensive laboratory studies which are time-consuming and costly. Hence, this method is not practicable for daily use, and particularly not for hair-dressers or beauticians.

It is also known (for example, from EP-A 0 702 232) to determine hair damage by use of anionic dyes.

This method, however, provides insufficient information about the structural condition of hair. Other known methods consist of determining the elongation factor of hair or the degree of copper absorption of the damaged hair. Such methods are described in U.S. Pat. Nos. 5,461,925 and 4,665,741. These methods are nonspecific and can give false-positive or false-negative results. Moreover, they are time-consuming and require costly equipment.

Because, on the one hand, a reliable recognition and evaluation of existing damage to keratin-containing materials is indispensable for effective and logical cosmetic treatment and, on the other, no practicable rapid test methods for this purpose, and no devices or agents suitable for carrying out such a method, are known, a great need exists for a rapid test and for devices and agents suitable for such a test.

SUMMARY OF THE INVENTION

The object of the present invention is to eliminate the drawbacks of the prior art and to provide a reliable method for recognizing and evaluating damage conditions in keratin-containing materials, particularly hair, and devices and agents needed for said method.

This objective was reached within the scope of the claims presented herein.

Surprisingly, we have now found that keratin-containing material, for example hair, damaged to different degrees reacts differently to enzymatic and/or chemical treatment in aqueous solution and that the liquid sample shows different degrees of turbidity depending on the degree of damage to the keratin-containing material.

Hence, one aspect of the present invention is a method for recognizing and determining the condition of a keratin-containing material, said method consisting of subjecting a sample of keratin-containing material, for example a sample of hair, in aqueous solution to enzymatic and/or chemical treatment and then examining, evaluating and determining the condition of the hair on the basis of the turbidity of the resulting aqueous solution. The condition of the hair can readily be determined with the aid of a comparative value (zero value or standard value). The comparative value can be obtained by subjecting the same amount of healthy hair to enzymatic and/or chemical treatment under the same conditions as those used for the hair test sample and determining the turbidity of the resulting liquid sample.

By the expression "determining the condition of keratin-containing materials" is meant, in particular, the determination of possible or expected damage to the material involved. In the following, the aqueous solution obtained after the enzymatic and/or chemical treatment of a sample of keratin-containing material, for example a hair sample, will be referred to as the "liquid sample".

The method of the invention combines a number of advantages. It represents a rapid test for determining the condition of keratin-containing materials which in a very short time provides reliable information concerning the current condition of keratin-containing materials permitting a diagnosis of said condition. The method affords reproducible results enabling the user to follow changes in the condition of the keratin-containing material over a longer period of time on the basis of objective criteria and to prepare a data file therefor.

The method of the invention can be applied particularly advantageously in the area od hair care or hair cosmetics. For the user and particularly the hair-dresser, this also opens up the possibility of flexible and individual cosmetic hair treatment aiming at causal hair care. The method permits optical or visual examination of the liquid sample and, hence, is simple to carry out. The agents and devices needed to this end are easy to handle. Because of the high reproducibility and possibility of carrying out a differentiated examination of the condition or degree of damage in keratin-containing materials combined with the ease of handling, the method of the invention and the devices and agents of the invention that are appropriate therefor represent an ideal solution for fast evaluation of hair quality in particular.

All enzymatic and/or chemical procedures can be used for the method of the invention as long as they bring about a proteolytic or hydrolytic decomposition of hair. Hence, the method of the invention comprises enzymatic and/or chemical treatment of a sample of keratin-containing material (for example a hair sample) based on a proteolytic or hydrolytic reaction. Suitable to this end are purely enzymatic treatments, purely chemical treatments or combined enzymatic/chemical treatments of the materials to be examined.

As for enzymatic methods, suitable are all enzymes from the group of proteases and proteinases (exo- and endopeptidases or exo- and endoproteases and mixtures thereof) known for this purpose and which are capable of catalyzing the degradation of keratin-containing material, at least one enzyme for the enzymatic (or enzymatic/chemical) treatment being present in the aqueous solution involved. The enzymes can be used alone or as a mixture. They include, for example, papain, pronase E, proteinase K, subtilisin or trypsin, as well as keratinases, for example from *Fervidobacterium pennavorans* (FRIEDRICH, A. B., and ANTRANIKIAN,. G., Appl. Environ. Microbiol. 62: 2875, 1996), from *Streptomyces pactum,* DSM 40530 (BOECKLE, B. et al., Appl. Environ. Microbiol. 61: 3705, 1995). from *Candida pulcherima* KSY 188-5 (GOTOCH, T., et al., Biosci. Biotechnol. Biochem. 59: 367, 1995) or from *Bacillus licheniformis* PWD-1 (LIN, X, Appl. Environ. Microbiol. 61 (4): 1469–1474 1995, CHENG S. W., Biosci. Biotechnol. Biochem. 59(12): 2239–2243, 1995). The use of special keratinases can be advantageous, because they can accelerate the proteolytic degradation of keratin-containing materials. For example, the keratinase from *Fervidobacterium pennavorans* is known to be able to bring about rapid decomposition of chicken feathers. (FRIEDRICH, A. B. and ANTRANIKIAN, G., Appl. Environ. Microbiol 62: 2875, 1996).

The enzymes suitable for the method of the invention are commercially available, for example papain (isolatable from *Carica papaya*) from Boehringer Mannheim, pronase E (isolatable from *Streptomyces griseus*) from Sigma (Deisenhofen) or proteinase K (isolatable from *Tritirachium album*) from Merck (Darmstadt).

As for purely chemical methods for the decomposition of keratin-containing materials, organic and/or inorganic reagents, which are capable of preferentially hydrolyzing keratin, are suitable and thus are keratolytically active and/or have reducing properties. Organic and inorganic reagents suitable for this purpose include reducing agents that can be used under basic as well as under acid conditions. The organic and inorganic reagents can be present in the aqueous solution, either alone or as a mixture. For example, partial aqueous reductive hydrolyses with, for example, urea-bisulfite solutions (for example a solution containing urea and sodium metabisulfite) in accordance with the IWTO (International Wool Textile Organization) specification (IWTO 11-62 (D), new edition, 1996), partial alkaline-aqueous hydrolyses with alkaline solutions, for example sodium hydroxide solutions in accordance with the IWTO specification (IWTO 4-60, new edition 1966), partial alcoholic-reductive hydrolyses with tributylphosphine and sodium iodide solutions according to KILPATRIK, D. J. et al., Text. Res. J. 40: 25, 1970), partial acidic-basic hydrolyses with performic acid-ammonia solutions, partial basic-reductive hydrolyses with thioglycolic acid-urea solutions or partial acidic-reductive hydrolyses with thioglycolic acid or cysteine glacial acetic acid solutions, such as cysteine, sodium metabisulfite, sodium sulfite, dithiothreitol (DTT) and dithioerythrol (DTE) are all suitable.

In this regard, the present invention also comprises a method characterized in that an aqueous solution of a sample of keratin-containing material, particularly a hair sample, is subjected to a chemical treatment and that the proteolytic or hydrolytic reaction underlying this treatment is carried out with the aid of at least one keratolytically active and/or reducing organic and/or inorganic reagent.

By combined enzymatic/chemical treatments of the keratin-containing material to be examined are meant treatments whereby the desired hydrolysis or proteolysis of the keratin-containing material takes place with the participation of both enzymes and purely chemical substances. In this case, the liquid sample in which the sample of the material (for example, the hair sample) is subjected to the enzymatic/chemical treatment contains at least one of the aforesaid enzymes together with at least one keratolytically active and/or reducing organic and/or inorganic reagent. Suitable to this end are, advantageously, amino acids or sulfites [for example cysteine, sodium metabisulfite, sodium sulfite, dithiothreitol (DDT) and dithioerythrol (DTE)].

Such a combined enzymatic/chemical treatment is a preferred object of the present invention.

Hence, a preferred method of the invention consists of subjecting an aqueous solution of a sample of the keratin-containing material, particularly a hair sample, to an enzymatic and chemical treatment and of carrying out the proteolytic or hydrolytic reaction underlying said treatment with the aid of at least one enzyme, as defined hereinabove, in combination with at least one keratolytically active and/or reducing organic and/or inorganic reagent, as defined hereinabove.

The enzyme can be added to the aqueous reaction solution first, followed by the organic and/or inorganic reagent, or the enzyme and the reagent can be used simultaneously, or the organic and/or inorganic reagent is added to the reaction solution first, followed by the enzyme. It can be advantageous to carry out the method by adding to the reaction solution first the organic and/or inorganic reagent and then the enzyme.

According to the invention, the examination and evaluation of the liquid sample can be carried out during and/or after the enzymatic and/or chemical treatment. In this regard, the invention comprises a method whereby the examination and evaluation of the liquid sample occur during and/or after the enzymatic and/or chemical treatment.

Naturally, the amounts of the enzymes and organic/inorganic reagents to be used depend on the choice of the enzymes and reagents, on the amount and type of sample of keratin-containing material and on the conditions under which the enzymatic and/or chemical treatment of the sample takes place (particularly the temperature and pH). In this respect, it should naturally also be kept in mind that enzymes can exhibit different temperature optimums and that the pH also affects the enzyme activity. The optimum conditions under which proteases, proteinases or peptidases exhibit their highest proteolytic activity are known to those skilled in the art. They can also be found in the abundant literature on this subject or they can be obtained from various enzyme providers. Moreover, the type of enzymes and the type and the amount of the other chemical reagents to be used depend on the time period within which the keratin-containing materials are to undergo proteolytic degradation so as to produce a desired turbidity in the liquid sample to be examined. Of course, the conditions under which a desired turbidity is obtained with specific amounts of enzymes and/or chemical reagents under specific conditions (temperature and pH) with a specific amount of hair sample can readily be determined by, and adapted to the needs of, those skilled in the art by carrying out comparative tests.

In general, it may be assumed that the enzymes to be used according to the invention can be employed in an amount (specific activity) from 1.0 to 500 U/mL, preferably from 5.0 to 250 U/mL and particularly from 5.0 to 35.0 U/mL. We were able to determine that a specific enzyme activity, particularly in conjunction with a hydrolytically acting, keratolytically active and/or reducing chemical reagent, in the range from 5.0 to 35.0 U/mL is sufficient to produce turbidity within 5 to 30 minutes, so that a reliable and reproducible determination of the condition of or damage to the keratin-containing materials, particularly hair damage, can be performed.

As regards the amount of the keratolytically active and/or reducing chemical reagents to be used according to the invention, no firm numbers can be stated because of the differences existing among the various possible reagents. By simple testing, however, it is easy to determine the desired amount for the proteolysis or hydrolysis of a sample of keratin-containing material and for attaining adequate turbidity for the determination of the condition of or damage to the material. We found it useful, however, to use the said inorganic chemical reagents in an amount from 0.5 to 50.0 mg/mL, preferably from 1.0 to 25.0 mg/mL and particularly from 2.0 to 15.0 mg/mL, advantageously in combination with an appropriate enzyme. As regards organic chemical reagents, for example cysteine (particularly L-cysteine), amounts between 0.1 and 50 mg/mL, preferably between 0.2 and 30 mg/mL and particularly between 0.5 and 25 mg/mL can be used. Higher cysteine concentrations in the aqueous solution (reaction solution) should be chosen particularly when cysteine is the only chemical reagent present, preferably in combination with an enzyme that is appropriate according to the invention. Small amounts of cysteine can be used advantageously when at least one other inorganic keratolytically active and/or reducing agent, for example one or more sulfites, is present together with cysteine, particularly in combination with an enzyme to be used according to the invention.

The presence of at least one inorganic chemical reagent (for example one or more sulfites) together with an organic chemical reagent (for example, cysteine), particularly in combination with an appropriate enzyme, is not necessarily required for optimum proteolytic degradation of a sample of keratin-containing material. We found that at low cysteine concentrations from 0.1 to 2.0 mg/mL the simple presence of at least one inorganic chemical reagent, for example a sulfite [for example, in a total amount of 10 mg of sodium metabisulfite (7.0 mg/mL) and sodium sulfite (3.0 mg) can cause the reaction rate to increase and the turbidity in the liquid sample to appear faster. Alternatively, the reaction rate and thus the turbidity can be increased by increasing the cysteine concentration. Advantageously, in this manner both the rate of appearance and the intensity of the desired turbidity can readily be controlled by varying the organic and inorganic reagents used.

The aqueous solution to be used for the method of the invention and in which the enzymatic and/or chemical treatment of a sample of keratin-containing material takes place has a pH in the range from 5.0 to 11.0, preferably from 5.0 to 9.0 and particularly from 5.5 to 7.5, depending on the reactants chosen (enzyme and/or organic and/or inorganic reagents) for the enzymatic and/or chemical treatment. With proteinase K, an advantageous pH range is from 5.5 to 7.5, with pronase E from 6.0 to 7.5 and with papain from 6.0 to 7.5. In general, an appropriate pH range is that from 5.5 to 7.5 in which advantageous proteolytic or hydrolytic decompositions of the sample of keratin-containing material and thus suitable turbidity can be achieved. For the said enzyme examples, a pH of 6.5 can be viewed as a guideline. When other enzymes are used, the pH optimums must, of course, be chosen accordingly.

Advantageously, the reaction mixture or the liquid sample which is in the form of an aqueous solution and in which the enzymatic and/or hydrolytic treatment of a sample of keratin-containing material takes place can contain a buffer system, for example a phosphate buffer. Suitable for this purpose is, for example, a sodium phosphate buffer (50 mM) of pH 6.5.

The temperature range in which the enzymatic and/or chemical reaction of the keratin-containing material takes place in the aqueous solution also depends on the reactants chosen for the enzymatic and/or hydrolytic treatment of the keratin-containing material. The temperature chosen should be between 20 and 100° C., preferably between 30 and 60° C. and particularly between 40 and 50° C.

We found that the rate and the extent of decomposition of the keratin-containing material, particularly of hair, increased with increasing temperature and that the turbidity increased accordingly. At a temperature of 50° C. and, for example, with a reaction mixture consisting of a proteolytic enzyme (for example papain) and a reducing agent (for example cysteine) in a phosphate buffer (50 mM), a hair sample decomposed rapidly. Here, too, as in the selection of the reactants (for example, variation in the amounts of cysteine and sulfites), it is possible to control the change in turbidity advantageously by selecting an appropriate reaction temperature.

Advantageously, the amount and length of the sample of keratin-containing material (for example, a sample of hair, wool, fiber or nails) are chosen so that they can be compared with a defined amount (in mg) and/or length (in cm) of a control (for example, of healthy material). The amount and length of the sample to be used can vary widely depending on the volume of the reaction vessel in which the enzymatic and/or chemical treatment takes place. Advantageously, the sample size of keratin-containing material can be between 0.01 and 100 mg, preferably between 0.5 and 50 mg and particularly between 1.0 and 10 mg. In the case of hair (or wool or fibers), the length of the hair sample can be between 0.05 and 5.0 cm, preferably between 0.1 and 1.0 cm and particularly between 0.1 and 0.5 cm. Smaller amounts (0.1 to 10 mg) and lengths (0.1 to 0.5 cm) should be advantageous when the measurement of turbidity is to be performed in a small volume (for example in small test tubes or cuvettes for photometric determinations). The amounts mentioned as examples correspond to the amounts mentioned in the foregoing as examples for the reactants used in the enzymatic and/or chemical treatment. Naturally, the amounts and lengths of the keratin-containing material can be increased or decreased depending on the prevailing conditions and the procedure to be used. Basically, it is advantageous not to use a hair length exceeding about 1.0 cm, because, in general, a shorter hair length can accelerate the proteolytic and/or hydrolytic degradation of hair and thus make it possible to obtain turbidities that can be evaluated within a very short time (<10 minutes).

The length of time needed for the formation of an appropriate turbidity for determining the condition of keratin-containing materials varies depending on the choice of the aforesaid parameters (reactants, pH, temperature and amount and length of the sample of keratin-containing material). The duration of the enzymatic and/or chemical treatment of the sample of keratin-containing material can vary from 1 minute to 30 minutes and preferably from 5 to 20 minutes. Various tests have shown that sufficient turbidity for the evaluation and determination of the condition of, for example, hair can be attained by the method of the invention within as little as 10 minutes.

Because the tests for carrying out the present invention were performed, in particular, on hair, the invention shall be explained in greater detail on the example of hair without thereby limiting the scope of the invention. The measures and the values and quantities described in the following can readily be applied and transferred also to other keratin-containing materials.

In general, we were able to establish that in the presence of an enzyme the extent of proteolytic degradation of hair samples varies within wide limits depending on the selection of appropriate organic or inorganic chemical reagents, pH and temperature. A higher reaction rate manifests itself in a reduction of the maximum attainable turbidity. For a slower reaction occurring within 10 to 1 5 min following the addition of the enzyme (for example, when papain and 20 mg/mL of cysteine are used at pH 5.5 and 50° C. or 10 mg/mL of DTE, pH 6.0, 45° C.), an increasingly linear curve is obtained. This can facilitate the evaluation. Hence, it is particularly advantageous when the reaction time to maximum turbidity is between 5 and 20 minutes and particularly between 7 and 15 minutes. We found that this method of carrying out the reaction is advantageous when the hair samples to be analyzed are expected to present considerable damage. The preferred conditions for the enzymatic/chemical treatment of hair samples are, for example, as follows: 5.0 mg of approximately 0.1-cm-long hair (21.1 U) plus cysteine (20 mg/mL), pH 6.5, 50° C. or papain (21.2 U) plus DTE (10 mg/mL), pH 6.2, 50° C.

For the analysis and evaluation of the turbidity obtained in the liquid sample according to the invention, it is disadvantageous if, after the enzymatic and/or chemical treatment of the hair, undecomposed hair components are present in the liquid sample. This could be a hindrance, for example, in the use of physical measuring methods, particularly in turbidimetric measurements with a photometer, and could lead to erroneous results. Hence, it is advantageous to remove hair components that have remained undecomposed by the enzymatic and/or chemical treatment before the examination or to keep them removed during the examination and to carry out the examination and evaluation of the liquid sample in the absence of undecomposed hair components. In many cases, particularly when instrumental methods of measurement are used (for example, extinction or turbidity measurements with a photometer) it will suffice to free of undecomposed hair components primarily that region of the liquid sample which contains the path of the radiation used for measuring the turbidity. Bottom sediments of undecomposed hair components have no major relevance in this case.

Before the examination of the liquid sample by a physical separation method, the undecomposed hair components can be removed for example by filtration, centrifugation or sedimentation or by the use of appropriate mechanical separation devices, for example sieves, nets, screens or filters. Such methods can readily be applied using small test tubes, measuring cells or measuring cuvettes, or the mechanical separation means can be permanently or removably built into such test tubes, cells or cuvettes. For example, the mechanical separation means built into the measuring cell may make it possible to separate the region of the liquid sample in which the enzymatic and/or chemical treatment of the hair is carried out from the region of the liquid sample used for the turbidity measurement. In this case, it can be advantageous if the measuring cell with integrated or inserted mixing system brings about uniform distribution of the hair components causing the turbidity.

Hence, according to the invention, a preferred method consists of removing, before examining the liquid sample, the components of the hair (or of the keratin-containing material) that remained unreacted during the enzymatic and/or chemical treatment or of keeping said components away during the examination so that the examination and evaluation of the liquid sample are carried out in the absence of undecomposed components of the hair (or of the keratin-containing materials).

It can be advantageous for the measurement and examination of the liquid sample if the transparent container (test tube, cell, cuvette) is made of glass or plastic material and if additionally it is fitted with a device for thermostatting the liquid sample. Such a device can consist of a heating band or a heated water bath.

The examination with the naked eye can be carried out, for example, by comparing a liquid sample obtained from an appropriately treated hair sample with the liquid sample obtained from undamaged hair (comparative or zero value), preferably in transmitted light. Such a method can be used particularly when, for example, only a rough evaluation of hair damage is desired.

According to the invention, examination by physical measuring methods is preferred, because it permits a more accurate evaluation and determination of damage to keratin-containing materials (for example, hair damage). Particularly preferred is a method whereby the examination and evaluation of the liquid sample is based on a turbidity measurement. Suitable to this end are all optical methods known to those skilled in the art, provided said methods make it possible to perform measurements on liquids containing undissolved, suspended particles. These include, for example, methods based on light scattering, nephelometric measurements (tyndallometry), fluorescent radiation measurements, transmitted light or extinction measurements and turbidimetric measurements (turbidimetry). According to the invention, turbidity measurement (turbidimetric measurement) of the liquid sample obtained is preferred.

The method of the invention based on physical measurement methods can be carried out by all instruments and agents known to those skilled in the art and which are commercially available. These include photometers in particular. Turbidity measurement with a photometer or turbidity photometer is preferred.

Hence, a preferred method comprises examining and evaluating the liquid sample by turbidimetric measurement with a photometer. Thereafter, the condition of the keratin-containing material (hair or hair damage) can readily be determined by comparison with a standard or zero value (preferably based on undamaged hair).

According to the invention, however, the use of a turbidity photometer for determining the condition of keratin-containing materials in one of the methods underlying the present invention is also included.

In the event that the condition of the keratin-containing material is examined, evaluated and determined by turbidimetric measurement, generally valid turbidity units must be used. Such turbidity units are either the values determined by measuring the attenuation of the radiation passing through the liquid sample (FAU, formazine attenuation unit) or those obtained by measuring the intensity of the scattered radiation (FNU, formazine nephelometric unit). The German "formazine turbidity unit" (TE/F) corresponds to the values determined by use of FNU.

According to the method of the invention, the examination and evaluation of the liquid sample can be carried out during and/or after the enzymatic and/or chemical treatment of the sample of keratin-containing material. The examination and evaluation of the liquid sample during and/or after the enzymatic and/or chemical treatment of the sample can be performed either indirectly and discontinuously or directly and continuously (on-line). By the discontinuous method, the turbidity of the liquid sample can be determined or measured on the basis of individual values at specific time intervals.

The continuous method whereby the turbidity or the change in turbidity in the liquid sample is followed directly and continuously (on-line) has the advantages of being less time-consuming because, for example, less pipetting is required. Moreover, such a method permits kinetic evaluation of the data. The method of the invention can thereby be further shortened, so that an evaluation and determination of the condition of the keratin-containing material can be performed in less than 10 minutes.

According to the invention, the continuous method is preferred. Such a method requires appropriate instrumentation consisting of a photometer in combination with a heating system that heats the transparent reaction vessel (measuring cell, test tube, cuvette) needed for the turbidity measurement, a mixing device inserted or built into the reaction vessel and a controllable drive, preferably an electric motor, for actuating the mixing device.

The heating system preferably consists of a controlled thermostatting system (thermocouple) and can consist, for example, of a heating band in contact with the reaction vessel.

The mixing device, which preferably is driven in controllable manner by an electric motor that is solidly connected with the photometer, can consist of a stirrer or of a syringe or disposable syringe which reaches into the measuring cell or into the reaction liquid contained therein. The rotating stirrer can be provided with appropriate stirring blades or it can consist of an angular or round rod made of metal, glass or plastic, which can have indentations, for example one having the shape of an auger. The stirring device, however, can also consist of a magnetic stirrer whereby the stirring is brought about by a stirring element present in the reaction liquid. When a syringe is used, said syringe can advantageously be provided at its lower end with a screen, sieve or net. The plunger or piston of the syringe can, by a constant up-and-down movement, keep the hair sample or the liquid sample in constant motion. This ensures that the sample of keratin-containing material in the reaction liquid is constantly kept in motion and that the enzymatic and/or chemical treatment of the sample of keratin-containing material is carried out under optimum conditions. The volume of the syringe in this case is the reaction space in which the enzymatic and/or chemical treatment of the sample of keratin-containing material takes place. The plunger can be moved up and down by means of a controlled electric motor. FIGS. 1a and 1b and FIG. 2 are schematic representations of suitable systems.

Those skilled in the art know that proteolytic and hydrolytic reactions can be influenced by the intensity at which the reaction liquid is mixed and that they can depend on the speed of the mixer or on the degree of movement of the mixing device. In general, it may be assumed that the rate and intensity of the proteolytic or hydrolytic decomposition of the keratin-containing material underlying the present invention increases with increasing speed of rotation or of movement of the mixing device. This parameter can be varied depending on the time interval within which a specified turbidity is to be attained. Rotational speeds of a magnetic stirrer or a rod-shaped stirrer with stirring blades or indentations from 100 to 10,000 rotations per minute (rpm), particularly from 500 to 5000 rpm and preferably from 500 to 2000 rpm have been found to be advantageous. The number of up-and-down movements of a plunger or piston in a syringe-type mixing device can range from 10 to 500 and particularly from 50 to 200.

Hence, a preferred method consists of subjecting the sample of keratin-containing material to an additional mechanical stress during the enzymatic and/or chemical treatment.

When the method of the invention and of the attendant recognition, evaluation and determination of the condition of the keratin-containing material is to be highly automated, the examination and evaluation of a liquid sample can be carried out by electronic means. Hence, the method of the invention also consists of performing the examination and/or evaluation of the liquid sample in computer-controlled manner and with the aid of a computer.

To this end, the described photometer system is advantageously connected to a computer, internal processor or "personal computer". In this manner, the data obtained by turbidimetric measurement can be stored and then evaluated at any time.

In addition, a recorder or printer can advantageously be connected to a photometer to provide a graphic representation of the turbidity variations or to print out numerical values. It is also possible to connect a video screen or display to the photometer to be able to obtain directly readable graphics or numerical values. Such data can be stored by means of a connected computer and, for example, retrieved at any time for comparison purposes and selectively printed by means of a connected printer. Any common computer, particularly a common personal computer (PC), can be used for this purpose.

Hence, another object of the method of the invention is characterized in that the examination and evaluation of the liquid sample is carried out with the aid of a computer and/or recorder and/or a video screen (display) and/or a printer.

The availability of an an apparatus for recognizing, determining and evaluating the condition of a keratin-containing material, which apparatus consists of a combination of components namely the photometer with the reaction vessel (for example a measuring cell, cuvette or test tube), a heating system for heating the reaction vessel of the photometer, a mixing device inserted or built into the reaction vessel and a controllable drive for moving the mixing device, is thus advantageous for carrying out the method of the invention.

Hence, another object of the invention is an apparatus for recognizing, determining and evaluating the condition of a keratin-containing material, which apparatus consists of a photometer with reaction vessel, with an adapter or support therefor, in combination with a heating system for heating the reaction vessel, a mixing device for mixing the liquid sample in the reaction vessel and a controllable drive for the mixing device. To maintain a constant temperature in the reaction vessel, the heating system can be connected with a thermocouple, and the heater can be in the form of a heating band. Such a heating band can be integrated with the adapters and supports for the reaction vessels, particularly the cuvettes or test tubes, to be used according to the invention and normally provided with photometers. The mixing device can consist of a syringe with a plunger or piston or of a stirrer which can be moved mechanically, electrically or magnetically or of an ultrasonic generator so that the mixing is ultrasound-induced.

Such an apparatus can advantageously be functionally connected with a recorder, printer, video screen (display) or computer, internal processor or personal computer (PC).

It may be advantageous for practical handling purposes if the apparatus of the invention is in the form of a mobile, compact unit. In particular, the computer can advantageously be in the form of a manual instrument which is spatially separated from the stationary photometer unit and is preferably connected to a recorder, printer or a video screen display, and can be used in mobile manner.

Because the use of an apparatus as that described hereinabove is advantageous for purposes of the invention, the present invention also includes the use of the described apparatus for identifying and determining the condition of a keratin-containing material in one of the methods of the invention.

It is advantageous for carrying out the method of the invention if both the appropriate equipment and the reagents required therefor are combined as a unit or in the form of a kit. Such a kit advantageously consists of a system as described hereinabove and includes a buffer solution, at least one enzyme and at least one proteolytically or hydrolytically active and keratinolytically effective and/or reducing chemical reagent. Such a combination (kit) has the advantage that all individual components are adapted to each other, that the user can carry out the method easily and on a routine basis and that reproducible and comparable results can be obtained at all times.

Another object of the present invention is therefore a kit for examining, evaluating and determining the condition of a keratin-containing material, said kit comprising a buffer solution, at least one enzyme and at least one proteolytically or hydrolytically active and keratinolytically effective and/or reducing chemical reagent. Advantageously, this kit can also contain a sample of a keratin-containing material, for example a sample of hair that has not been cosmetically treated and/or a liquid sample serving as standard, blank or zero value. In addition to the above-indicated components, such a kit can also include the apparatus underlying the present invention.

The use of a kit such as that described in the foregoing for recognizing and determining the condition of keratin-containing materials by a method according to the invention is advantageous and therefore is also an object of the present invention.

BRIEF DESCRIPTION OF THE DRAWING

The objects, features and advantages of the invention will now be illustrated in more detail with the aid of the following description of the preferred embodiments, with reference to the accompanying figures.

DETAILED DESCRIPTION OF THE INVENTION

The following examples illustrate the invention in greater detail.

EXAMPLES

Figure 2:
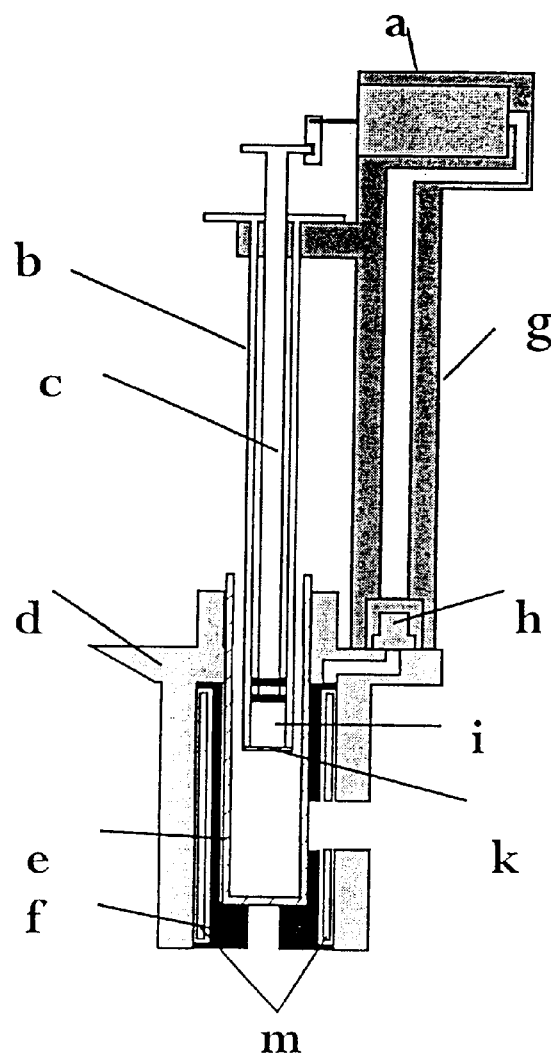

FIG. 2 is a schematic cross-sectional view through an alternative embodiment of an apparatus for direct (on-line) determination of the turbidity of liquid samples containing hair in combination with a photometer, wherein a=electric motor, b=disposable syringe, c=plunger, d=adapter for glass cuvette, e=glass cuvette, f=aluminum block, g=cap, h=plug, i=reaction space, k=screen, m=heating band.

Figure 3:
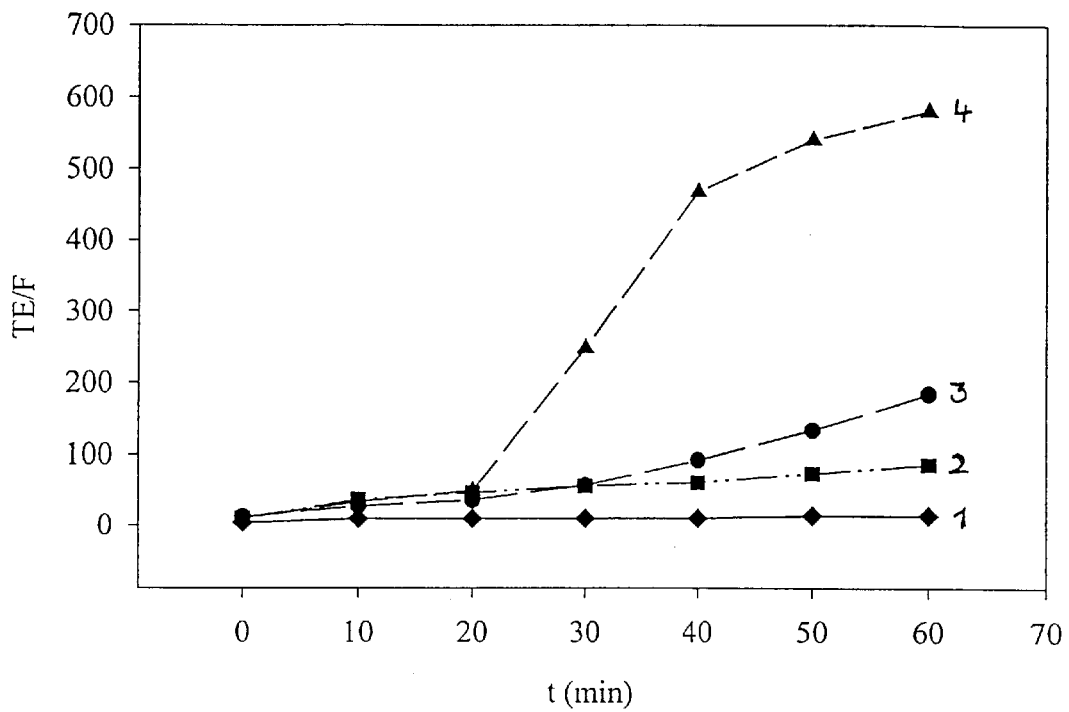

FIG. 3 is a graphical illustration of turbidity measurement results showing proteolytic decomposition of liquid samples containing hair of two different degrees of oxidation by turbidimetric photometry, in which 1=blank, non-oxidized hair, 2=non-oxidized hair, 3=once-oxidized hair, 4=3 times oxidized hair. Test conditions: 50 mg of hair (1.0 cm-long); 100 µL (21.2 U) of papain; 5.0 mL of 50 mM sodium phosphate buffer, pH 6.5 (reaction volume, liquid); 0.74 mg/mL of L-cysteine; 7.0 mg/mL of $Na_2S_2O_5$; 3.0 mg/mL of $Na_2SO_3$; 45° C.; stirrer speed 600 rpm (magnetic stirrer). In each case, the result of a single determination was plotted.

Figure 4:
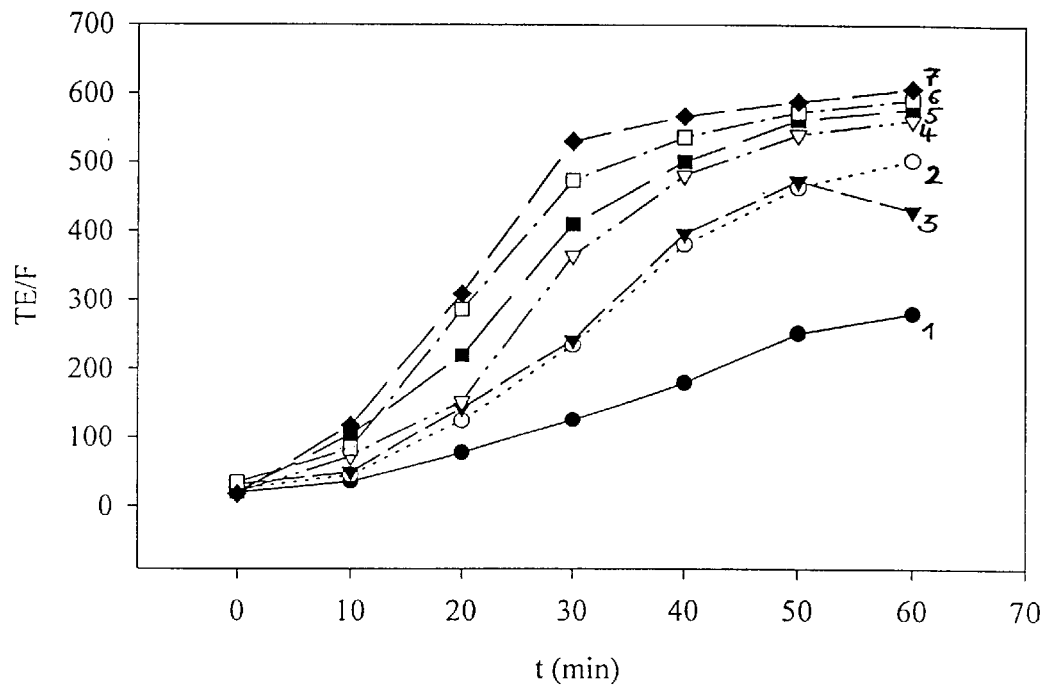

FIG. 4 is a graphical illustration of turbidity measurement results showing proteolytic decomposition of liquid samples containing hair of seven different degrees of oxidation by turbidimetric photometry, in which 1=once-oxidized, 2=twice-oxidized, 3=3-times oxidized, 4=4-times oxidized, 5=5-times oxidized, 6=6-times oxidized, 7=7-times oxidized hair. Test conditions were the same as in FIG. 3 with the exception that 0.5-cm-long hair was used. In each case, the result of a single determination was plotted.

Figure 5:
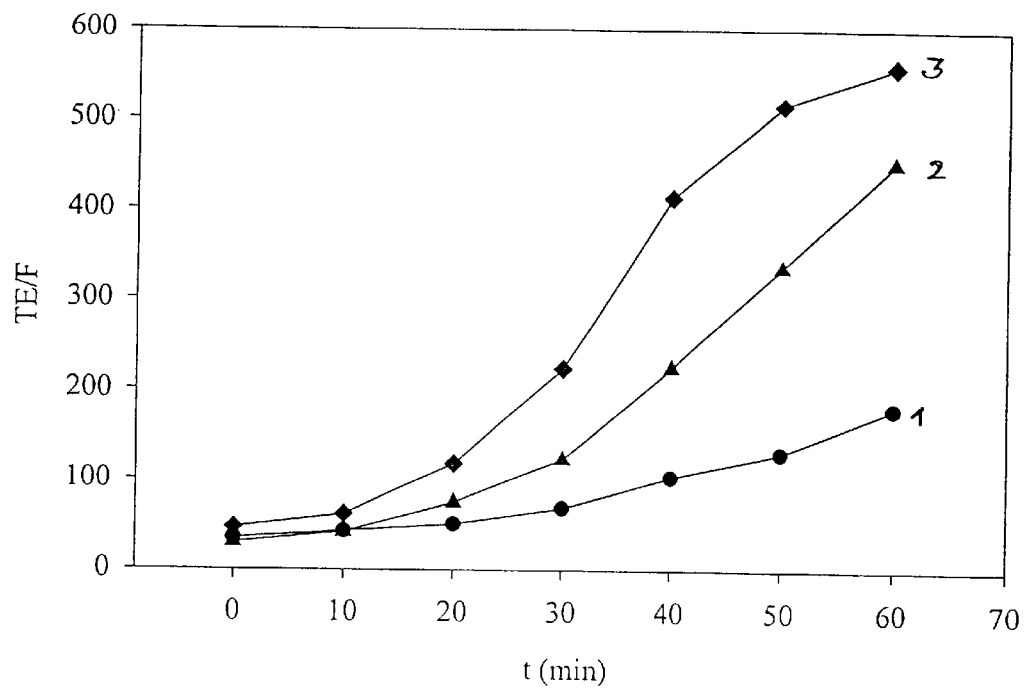

FIG. 5 is a graphical illustration of results of turbidimetric photometry of the proteolytic decomposition of samples of hair subjected to permanent wave treatment a different number of times. Number of permanent wave treatments: 1=one, 2=two, 3=six. Test conditions as in FIG. 3 with the exception that 0.3-cm-long hair was used. In each case, a single determination was plotted.

Figure 6:
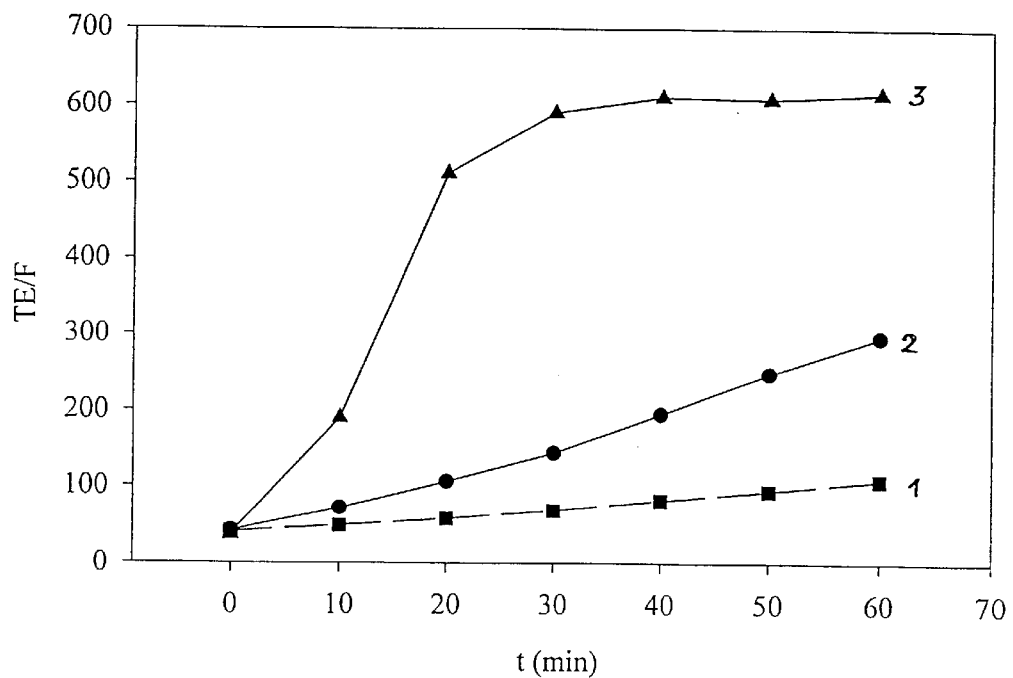

FIG. 6 is a graphical illustration of turbidity measurement results showing optimization of the proteolytic decomposition of hair samples of different degrees of oxidation, in which 1=unoxidized hair, 2=once-oxidized, 3=3-times oxidized hair. Test conditions were the same as in FIG. 3 with the exception that 50 mg of 0.3-cm-long hair and 500 µL (108 U) of papain were used.

Figure 7:
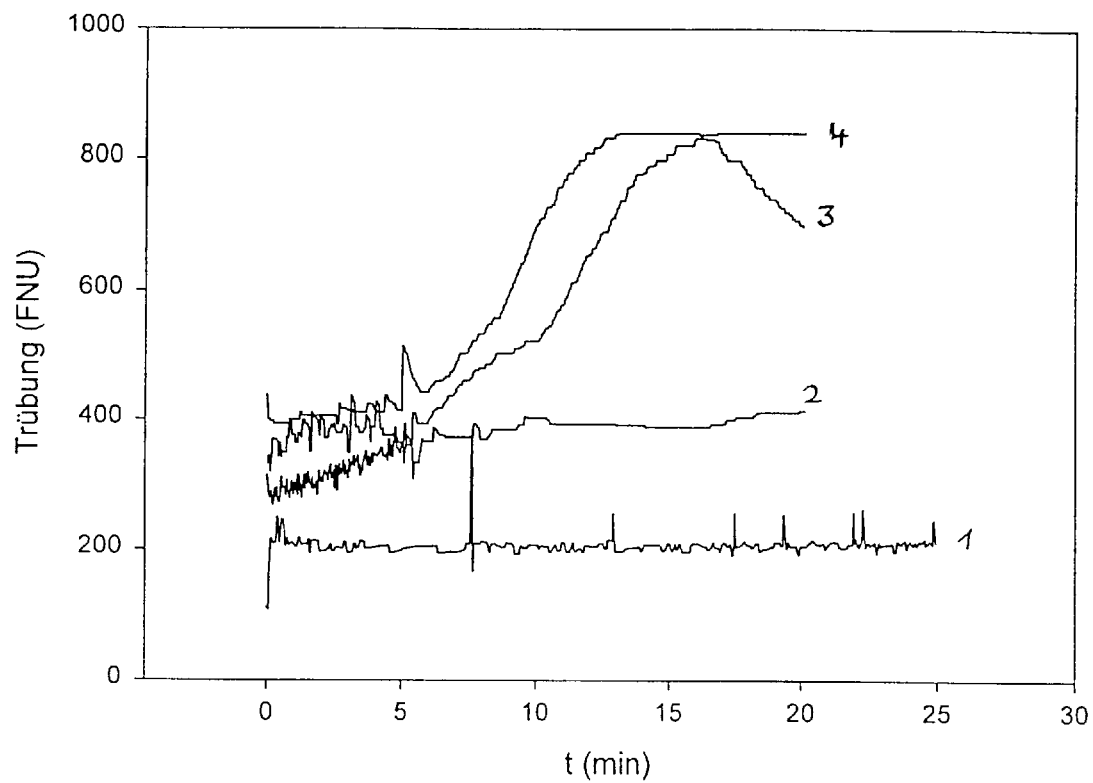

FIG. 7 is a graphical illustration of results of direct, continuous (on-line) measurement of turbidity in the proteolysis of oxidized hair samples, in which 1=unoxidized hair, 2=once-oxidized, 3=twice-oxidized, 4=3-times oxidized hair. Test conditions: 0.5 mg of hair sample (0.1 cm-long); 100 µl (21.2 U) of papain; 3.0 mL of 50 mM sodium phosphate buffer, pH 6.2 (reaction volume, liquid); 10 mg/mL of DTE; 50° C.; stirrer speed 1000 rpm.

Figure 8A:
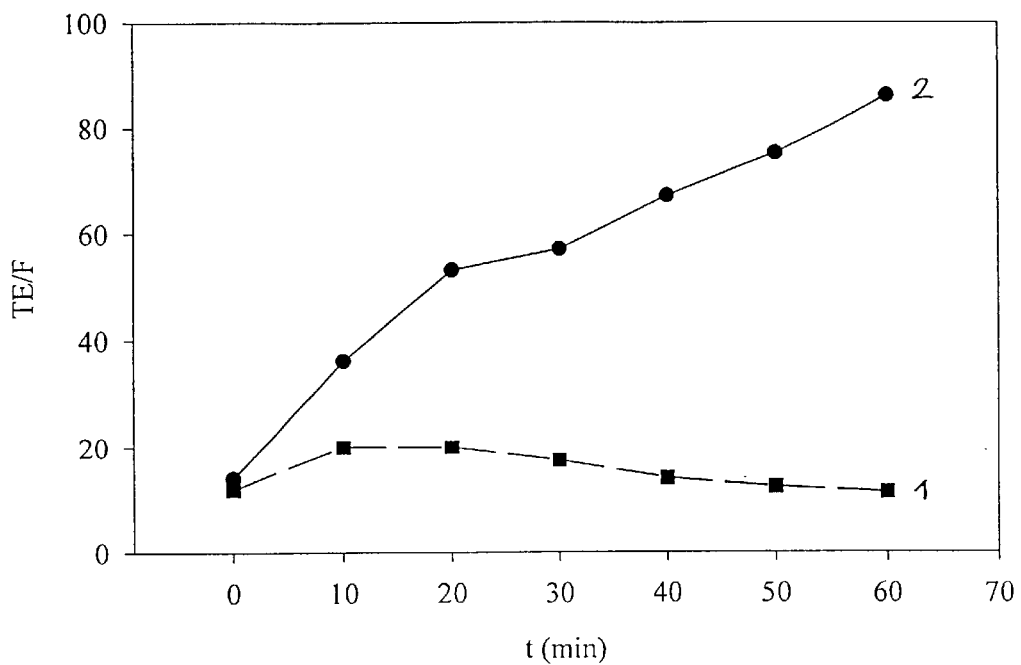
Figure 8B:
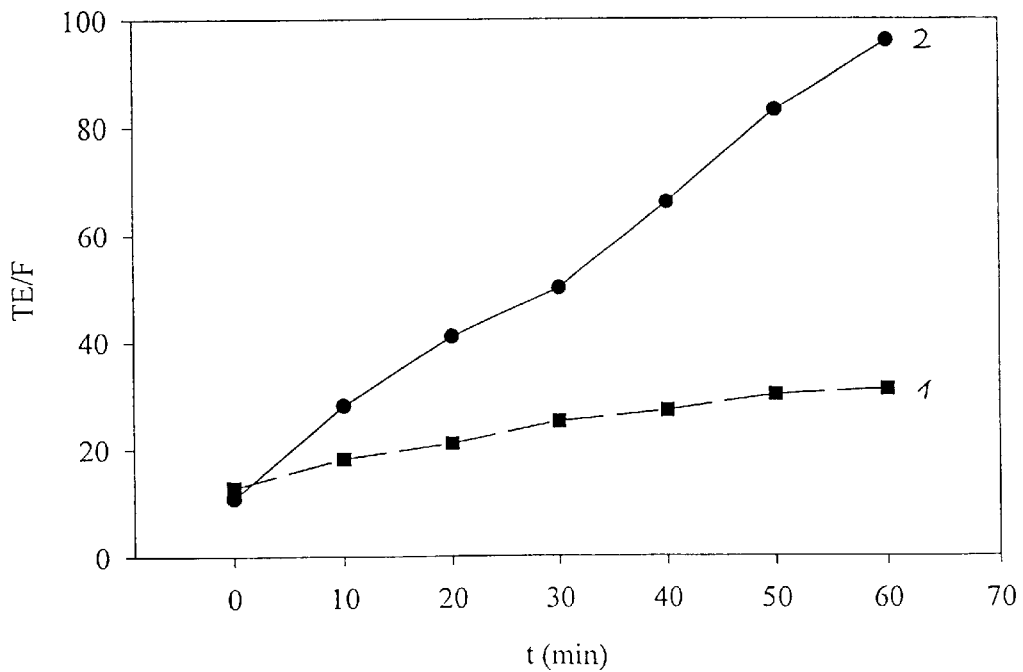

FIGS. 8a and 8b are graphical illustrations of turbidity measurement results showing a comparison of the proteolytic decomposition of weathered and nonweathered, untreated hair samples of dark-brown 18a) and blond hair (8b), in which 1=hair roots, 2=hair tips. Test conditions for 8a and 8b: 50.0 mg of hair sample (0.5-cm-long); 100 /μL (21.2 U) of papain; 5.0 mL of 50 mM sodium phosphate buffer, pH 6.5 (reaction volume, liquid); 0.74 mg/mL of L-cysteine; 7.0

Example 1

Oxidative Treatment of Hair Samples

To prepare hair oxidatively damaged to different degrees, hair from Central European women was sorted according to color and density and made into tresses without hair roots and tips (in each case, 3 g of 15.0-cm-long hair). Table 1 shows the degrees of oxidation and chemical treatment of the hair.

TABLE 1

| Degree of Oxidation | Chemical Treatment |
| --- | --- |
| Oxidized once | 30 min with 6% $H_2O_2$ |
| Oxidized twice | 2 × 30 min with 6% $H_2O_2$ |
| Oxidized 3 times | 3 × 30 min with 6% $H_2O_2$ |
| Oxidized 4 times | 4 × 30 min with 6% $H_2O_2$ |
| Oxidized 5 times | 5 × 30 min with 6% $H_2O_2$ |
| Oxidized 6 times | 6 × 30 min with 6% $H_2O_2$ |
| Oxidized 7 times | 7 × 30 min with 6% $H_2O_2$ |

Hydrogen peroxide was mixed in a 1:3 ratio with a bleaching powder [50.0% of ammonium per-sulfate, 23.0% of $NaHCO_3$, 25.5% of sodium silicate, 0.5% of $SiO_2$ (Aerosil 300, Degussa), 1.0% of EDTA].

Example 2

Permanent Wave Treatment of Hair Samples

To prepare hair damaged to different degrees by permanent wave treatment, tresses of the same origin and type as described in Example 1 were subjected to permanent wave treatment once, three times and six times.

To this end, the tresses were thoroughly moistened, dabbed with an absorbing towel and conditioned overnight at 95–100% relative humidity. Permanent wave lotion containing 8 w % of thioglycolic acid was applied uniformly to the conditioned tresses. The tresses were placed in a plastic pouch and kept in a drier at 45° C. for 15 minutes. At the end of the exposure period, the tresses were washed with warm running water at 37° C. and then dipped into a fixing solution (3% $H_2O_2$) for 3 minutes. The tresses were then removed from the fixing bath and allowed to stand 7 minutes. The treatment was completed by a 5-min final soaking in warm water at 37° C. and then dried 30 min with circulating air at 45° C.

For a three-fold and six-fold permanent wave treatment, this procedure was repeated the requisite number of times with 24-hour intervals between individual treatments.

Example 3

Untreated, Weathered Hair Samples

The starting material were pigtails of untreated brown and blond hair of Central European women which hair had been exposed to normal weather influences. To ensure sufficient weathering, hair at least 20-cm-long was used. The hair was removed from the head just before the proteolytic or hydrolytic treatment was applied. In each case, a comparison was made between hair roots (no weathering) and hair tips exposed to environmental conditions.

Example 4

Determination of the Degree of Turbidity

To determine the degree of turbidity, 1.0 mL of liquid (liquid sample) was removed from the preparation containing the proteolytically treated hair and analyzed with a Nephla LPG 23 turbidity photometer (Dr. Bruno Lange GmbH, Berlin) provided with a cuvette adapter and a glass cuvette (11 mm). The photometer had permanent calibration constancy and its accuracy at the calibration point of 10 FNU (TE/F) was <2% [sic—Translator]. The analyzed sample was then returned directly to the reaction vessel (glass cuvette, measuring cell) for further measurements. To obtain the blank value, a reading was obtained in the absence of hair on 1.0 mL of the buffer (50 mM sodium phosphate buffer, pH 6.5) plus the reducing agent (L-cysteine, DTT or DTE) and the enzyme (papain, pronase E or proteinase K).

By means of the turbidity photometer with a cuvette (measuring cell), turbidity measurements were made up to a temperature of <60° C. (temperature of the reaction mixture). After calibration, the turbidity was selectively plotted against FNU, TE/F or mg/L of $SiO_2$ in accordance with the $DIN^2$ formazine standard. The same was true for the modified device of Example 5.

Example 5

Apparatus for Direct, Continuous Measurement of Turbidity

Figure 1A:
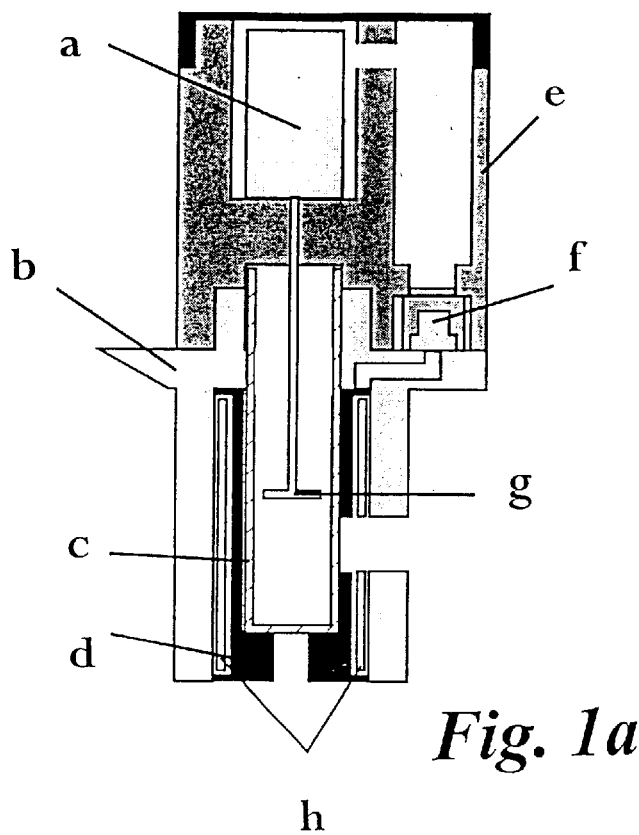
FIGS. 1a and 1b are schematic cross-sectional views through two embodiments of apparatuses for direct (on-line) determination of the turbidity of liquid samples containing hair in combination with a photometer, wherein a=electric motor, b=adapter for glass cuvette, c=glass cuvette, d=aluminum block, e=cap, f=plug, g=stirrer; h=heating band. mg/mL of $Na_2S_2O_5$; 3.0 mg/mL of $Na_2SO_3$; 45° C.; stirrer speed 600 rpm (magnetic stirrer). In each case, a single determination was plotted.
Figure 1B:
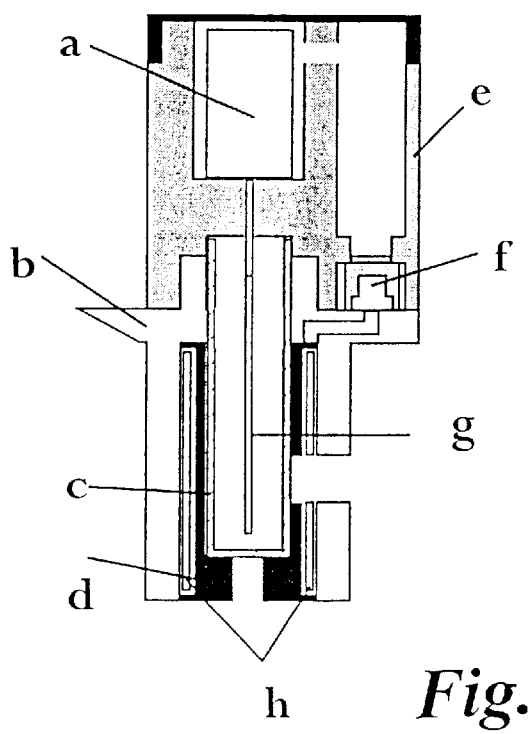

To be able to follow the proteolytic degradation of hair samples continuously and directly (on-line), the turbidity photometer of Example 4 was modified by building into it a heating band and a stirring unit. To this end, the wall of the cuvette adapter for the 11-mm round cuvettes was integrated with a heating band (HR 5377R17.5L 12A, supplied by Telemeter Electronic GmbH) and a thermocouple (RS 219-4719, supplied by RS Components GmbH) which were controlled by means of a controller (CAL 3200, supplied by CAL-Controls). The stirring unit consisted of a stirrer which reached into the cuvette (wood auger 1.5 mm in diameter) and which was actuated by an electric motor (SP 200 EC 3-5V DC, supplied by SP. J. Schwarzer GmbH). The controller and the electric motor were designed for low voltage and were supplied with power from a transformer. FIGS. 1a and 1b are schematic representations of such a device, and FIG. 2 shows an alternative device.

Example 6

Standardization of Hair Samples

Before the actual enzymatic treatment to create standardized baseline conditions for tests involving proteolytic decomposition of the hair samples to be examined, the hair was washed in standard fashion for 2 hours with 1% sodium dodecylsulfate (SDS). It was then carefully rinsed with distilled water and dried in a drier at 37° C. for 12 hours.

Example 7

Proteolytic Decomposition of Once- and 3-Times-Oxidized Hair Samples with Papain Papain is a nonspecific endopeptidase (thiolprotease) from *Carica papaya* with esterase and trans-aminase activity. Its temperature optimum was 50° C. and the pH optimum between 6.0 and 7.0 (EC 3.4.22.2). The enzyme was supplied by Boehringer Mannheim (Product No. 1 693 379) in the form of a suspension (10 mg/mL).

Before the treatment with papain, 50.0 mg samples of each of unoxidized, once-oxidized and 3-times oxidized hair (as in Example 1) of 1.0 cm length were suspended or preswollen in a total volume of 5.0 mL of sodium phosphate buffer (50 mM, pH 6.5) in a closed glass tube for 1 h at 45° C. To activate the protease and to reduce the disulfide bridges of the hair, L-cysteine (0.74 mg/mL), sodium metabisulfite (Na$_2$S$_2$SO$_3$) and sodium sulfite (Na$_2$SO$_3$, 3 mg/mL) were added. After the addition of 100 μL (21.6 U) of a papain suspension (10 mg/mL), the turbidity was determined with a Nephla LPG 23 turbidity photometer (Example 4). The reaction was carried out with stirring (magnetic stirrer, 600 rpm) at 45° C. The blank value was that obtained for a hair sample in buffer solution containing the reducing agent but no papain. In each case, a single determination was plotted.

The reagents L-cysteine, sodium metabisulfite and sodium sulfite were supplied by Sigma (Deisenhofen). FIG. 3 shows the results obtained. It is quite evident that the two samples of hair with different degrees of oxidation gave a different increase in turbidity. After as little as 40 min, all hair samples with different degrees of oxidation could be differentiated in terms of their turbidity behavior. The turbidity of the unoxidized hair increased only very slightly, whereas that of the three times-oxidized hair increased after 20 min much more than that of the once-oxidized hair sample. The blank showed no increase in turbidity at all. It is clear that the turbidity behavior depends on and correlates with the condition of the hair or the degree of hair damage.

Example 8

Proteolytic Decomposition with Papain of Hair Samples Oxidized up to Seven Times In analogy to Example 7, the turbidity of hair samples of seven different degrees of oxidation was determined as described in Example 1. In this case, we used samples of shorter, 0.5-cm-long hair (50 mg each) to increase the rate of reaction. In each case, a single determination was plotted.

FIG. 4 shows the results of this test series. After 20 minutes, it was possible to differentiate the differently pretreated hair samples, the degree of turbidity increasing with the extent of oxidation. It is evident that the turbidity behavior depends on and correlates with the condition of the hair or the degree of hair damage.

Example 9

Proteolytic Decomposition with Pronase E of Samples of Hair Oxidized Once, Twice and Three Times Pronase E is a nonspecific enzyme mixture of endo- and exoproteases from *Streptomyces griseus*. Its temperature optimum was 35–40° C. and the pH optimum 6.0–7.5 (EC 3.424.4k). The preparation obtained from Sigma, Deisenhofen, had a specific activity of 5.3 U/mg.

Before treatment with pronase E, in analogy to Examples 7 and 8, 50.0-mg each of unoxidized and once, twice and three times oxidized hair samples (as in Example 1) 1.0 cm in length were suspended or preswollen in a total volume of 5.0 mL of sodium phosphate buffer (50 mM, pH 7.5) or tris/HCl buffer (50 mM, pH 7.5) in a closed glass tube for one hour at 37° C. After addition of 2.0 mg (or 4 mg) of pronase E (10.6 or 21.2 U), the glass tubes were allowed to incubate at 37° C. with stirring (magnetic stirrer, 600 rpm) in a water bath, and as in Examples 7 and 8 the turbidity was determined with a Nephla LPG 23 turbidity photometer (Example 4). Here, too, marked differences in turbidity were attained depending on the differences in hair condition (hair damage).

By selecting a higher concentration of pronase E (4.0 mg, corresponding to 21.2 U), the decomposition of the hair sample was accelerated.

Example 10

Proteolytic Decomposition with Proteinase K of Samples of Hair Oxidized Once, Twice and Three Times Proteinase K is a serine endopeptidase obtained from *Tritirachium album* which preferably hydrolyzes the peptide bonds after the carboxyl group of N-substituted, hydrophobic, aliphatic and aromatic amino acids. The optimum temperature range of the proteinase K used (Merck, Darmstadt) was 25–35° C. and the optimum pH 6.5–7.5 (EC 3:4.21.14d). The enzyme activity of the suspended proteinase K was 600 U/mL. To activate this proteinase, it was also necessary to add Ca$^{2+}$ (BAJORATH, J. et al., Eur. J. Biochem. 176: 441, 1988)

Before treatment with proteinase K, in analogy to the preceding examples, 50.0-mg each of unoxidized and once, twice and three times oxidized hair samples (as in Example 1) 0.5 cm in length were.+suspended o r preswollen in a total volume of 5.0 mL of 50 mM tris/HCl buffer, pH 7.5, containing 2 M Ca$^{2+}$ (pH 7.5) in a closed glass tube for one hour at 25° C. After addition of 71 μL of proteinase K (42.2 U), the glass tubes were allowed to incubate at 25° C. with stirring (magnetic stirrer, 600 rpm) in a water bath, and as in the preceding examples the turbidity was determined with a Nephla LPG 23 turbidity photometer (Example 4). Here, too, marked differences in turbidity were attained depending on the differences in hair condition (hair damage).

Example 11

Proteolytic Decomposition with Papain of Hair Samples Subjected to Permanent Wave Treatment Once, Three Times and Six Times As in Examples 7 to 10, hair with varying degrees of permanent wave treatment was subjected, as in Example 2, to proteolytic digestion with papain, and the increase in turbidity was used to interpret the hair condition or hair damage. To this end, 50 mg of 0.5-cm-long hair was used.

FIG. 5 provides a graphic representation of the results with a single determination plotted in each case. Definite differences in turbidity were produced by hair subjected to permanent wave treatment a different number of times, and these differences correlated with the condition of the hair (hair damage).

Example 12

Comparison of Proteolytic Decomposition of Weathered and Nonweathered, Untreated Hair Samples of Dark-Brown and Blond Hair To determine the damage induced by weathering, the turbidity of samples of hair roots and hair tips were compared to each other. Dark-brown and blond hair was used for this purpose to establish how turbidity is affected by the hair color or the color pigments released by the enzymatic degradation, which in the case of dark-brown hair is eumelanine and in that of blond hair pheomelanine. These tests were carried out as in Example 7 by using in each case a 50.0-mg sample (0.5-cm long) of hair roots and hair tips for each of the two types of hair color. In each case, the result of a single determination was plotted. FIG. 8a (dark-brown hair) and FIG. 8b (blond hair) show the results obtained.

The curves indicate that weathered hair (hair tips) more readily underwent proteolytic degradation and, hence, produced more pronounced turbidity than nonweathered hair (hair roots). Differentiation of the two types of hair was possible after 10 minutes. Moreover, we found that the different hair colors and hair thicknesses had no effect on the turbidity measurement.

Based on tests with cosmetically treated hair (oxidized and permanently waved), we found that the proteolytic degradation of weathered hair was slower than that of cosmetically treated hair. From this we can conclude that the damage induced by weathering is mainly limited to the cuticula, whereas cosmetic treatment causes structural changes in the cortex as well (ROBBBINS, C. R. & BAHL, M. J., J. Soc. Cosmet. Chem. 35:379, 1984).

Example 13
Comparative Studies of Various Hair Samples

A comparison was made of all turbidity values obtained for the tested samples of untreated (naturally weathered) hair, oxidized hair, hair that had been subjected to permanent wave treatment and dark-brown and blond hair. All turbidity values were measured after 30 min incubation of 50 mg of hair with: 100 μL of papain; 5.0 mL of 50 mM sodium phosphate buffer, pH 6.5; 0.74 mg/mL of L-cysteine; 7.0 mg/mL of $Na_2S_2O_5$; 3.0 mg of $Na_2SO_3$; 45° C.; stirrer speed (magnetic stirrer) 600 rpm. The hair samples were 0.5 cm long with the exception of hair type No. 6 in which case the length of the hair sample was 1.0 cm. The test and reaction conditions were as in Example 7. Table 2 shows the turbidity values obtained for the samples of the various hair types. Hair taken at the roots and hair taken at the top represent unweathered and weathered hair, respectively. The percentages refer to the concentration of the $H_2O_2$ used for the oxidative treatment carried out as in Example 1.

TABLE 2

| No. | Hair Type | Turbidity (TE/F) |
|---|---|---|
| 1 | Dark-brown pigtail, untreated (hair roots) | 20 |
| 2 | Blond pigtail, untreated (hair roots) | 20 |
| 3 | Dark-brown tresses, unoxidized | 50 |
| 4 | Dark-brown pigtail (hair tips) | 60 |
| 5 | Blond pigtail (hair tips) | 60 |
| 6 | Dark-brown tresses once subjected to perm. wave treatment | 70 |
| 7 | Dark-brown tresses twice subjected to perm. wave treatment | 120 |
| 8 | Dark-brown tresses, oxidized once (6%) | 130 |
| 9 | Dark-brown tresses, 3 times subjected to perm. wave treatment | 230 |
| 10 | Dark-brown tresses, oxidized twice (6%) | 240 |
| 11 | Dark-brown tresses, oxidized 3 times (6%) | 240 |
| 12 | Dark-brown tresses, oxidized 4 times (6%) | 360 |
| 13 | Dark-brown tresses, oxidized 5 times (6%) | 410 |
| 14 | Dark-brown tresses, oxidized 3 times (9%) | 430 |
| 15 | Dark-brown tresses, oxidized 6 times (6%) | 470 |
| 16 | Dark-brown tresses, oxidized 7 times (6%) | 530 |

The samples of hair roots from the pigtails studied showed the lowest degree of damage. The weathered dark-brown and blond hair tips were only insignificantly more damaged (TE/F=60) than the dark-brown tresses of type-3 hair (TE/F=50) which served as a control for the treated hair samples. The hair that had received permanent wave treatment showed less damage compared to the oxidized hair. Thus, hair subjected to three permanent wave treatments (No. 9) showed about the same damage as twice-oxidized hair (No. 10). A marked difference was noted between more strongly bleached hair (9% $H_2O_2$) and less strongly bleached hair (6% $H_2O_2$), both oxidized three times (TE/F=430 vs. 240).

Example 14
Optimization of Proteolytic Decomposition

In contrast to the foregoing examples, hair samples were cut to a 0.3-cm length and treated with 500 μL (108 U) of papain. Unoxidized, once-oxidized and 3 times-oxidized hair samples were used. The oxidations were carried out as in Example 1. The test and reaction conditions were otherwise the same as in Example 7. FIG. 6 shows the results obtained. By increasing the papain content to 108 U per test and by reducing the hair length from 1.0 and 0.5 cm to 0.3 cm, the proteolytic degradation was accelerated even further, so that hair damage could be differentiated after as little as 10 minutes.

Example 15
Direct, Continuous Measurement of Turbidity Caused by Proteolysis of Oxidized Hair Samples 5.0 mg each of unoxidized, once and 3 times oxidized, 0.1-long hair was suspended in a total volume of 3.0 mL of 50 mM sodium phosphate buffer, pH 6.2, in a 10-mm glass cuvette. 10.0 mg/mL of DTE (Sigma, Deisenhofen) was added to activate the protease and reduce the disulfide bridges of the hair. After the reaction temperature of 50° C. was reached, 100 μL (21.2 U) of a papain suspension (10 mg/mL) was added, and the turbidity was determined directly and continuously with the photometer described in Example 5. The reaction and the continuous measurement were performed with constant stirring (1-mm auger, 1000 rpm). FIG. 7 shows the curves obtained for the hair samples examined.

After less than 10 min, the individual hair samples could definitely be differentiated.

Example 16
Reproducibility of Turbidity Measurements

The reproducibility of the turbidity measurements was checked under identical conditions using two preparations each of unoxidized and 3 times-oxidized hair samples (as in Example 1). The procedure was the same as in Example 7. Only the average value of the duplicate determinations was plotted. The result indicates that the error for a duplicate determination is <5%.

Example 17
Effect of the Reducing Agent on Turbidity Behavior in the Proteolytic Decomposition of Hair Samples Reducing agents, for example sulfites and L-cysteine, were used to activate the protease papain. Sulfites and L-cysteine penetrate the hair by diffusion and reduce the disulfide bridges. In the presence of L-cysteine and sulfites, the sodium alkylthiosulfate ("Bunte salt") is formed (CLARK, H. T., J. Biol. Chem. 97: 235, 1932). Whether this change in the tertiary structure has an effect on or accelerates the proteolytic degradation of hair was tested. To this end, to each preparation of unoxidized and 3 times-oxidized hair (50.0 mg each, 0.5-cm-long) [we added] the amounts of sulfite used in the examples (7.0 mg/mL of sodium metabisulfite, $Na_2S_2O_5$, 3.0 mg/mL of sodium sulfite, $NaSO_3$) were added together with L-cysteine (0.74 mg/mL) (Solution A). Alternatively, the sulfite was omitted and only L-cysteine was added at a concentration of 10.68 mg/mL) (Solution B). The reaction volume (liquid), the amounts of papain and sodium phosphate buffer (pH 6.5), the temperature and stirrer speed were the same as in Example 7.

We found that the preparations with sulfites (Solution A) and without sulfites (Solution B) differed only insignificantly.

Examples 18–77
Different Enzymatic/Chemical Treatments of Hair Samples with Papain The proteolytic decomposition of hair samples according to the following examples was carried out in a total volume (liquid) of 3.0 mL. The hair treatments (oxidations, permanent wave treatments, weathering) were carried out as in Examples 1, 2 and 3. The decompositions were carried out by the method of Example 6 and Example 7.

| Example | Hair Sample | Hair Treatment | Temp. | pH | Papain (U) | Reducing Agent | Remarks |
|---|---|---|---|---|---|---|---|
| 18 | 2.0 mg, 1.0 mm | 3-times oxidized | 45° C. | 6.5 | 21.6 | 0.74 mg/ml Cys, 7 mg/ml Na2SO5, 3 mg Na2SO3 | V[1] |
| 19 | 5.0 mg, 1.0 mm | 3-times oxidized | 45° C. | 6.5 | 21.6 | 0.74 mg/ml Cys, 7 mg/ml Na2S2O5, 3 mg Na2SO3 | V |
| 20 | 5.0 mg, 1.0 mm | 3-times oxidized | 45° C. | 6.5 | 21.6 | 10 mg/ml DTT | V |
| 21 | 5.0 mg, 1.0 mm | not oxidized | 45° C. | 6.5 | 21.6 | 10 mg/ml DTT | V |
| 22 | 5.0 mg, 1.0 mm (W)[2] | 3-times oxidized | 45° C. | 6.5 | 21.6 | 10 mg/ml DTT | V |
| 23 | 5.0 mg, 1.0 mm (W) | 3-times oxidized | 45° C. | 8.0 | 21.6 | 10 mg/ml DTE | V |
| 24 | 20 mg, 1.0 mm (W) | 3-times oxidized | 45° C. | 8.0 | 21.6 | 10 mg/ml DTE | V |
| 25 | 10 mg, 1.0 mm (W) | 3-times oxidized | 45° C. | 6.5 | 21.6 | 10 mg/ml DTE | V |
| 26 | 5.0 mg, 1.0 mm (W) | 3-times oxidized | 45° C. | 6.5 | 21.6 | 10 mg/ml DTE | V |
| 27 | 5.0 mg, 1.0 mm (W) | 3-times oxidized | 45° C. | 7.0 | 21.6 | 10 mg/ml DTE | V |
| 28 | 5.0 mg, 1.0 mm (W) | 3-times oxidized | 45° C. | 7.0 | 21.6 | 10 mg/ml DTT | V |
| 29 | 5.0 mg, 1.0 mm (W) | 3-times oxidized | 45° C. | 6.0 | 21.6 | 10 mg/ml DTE | V |
| 30 | 5.0 mg, 1.0 mm (W) | 3-times oxidized | 45° C. | 6.2 | 21.6 | 10 mg/ml DTE | V |
| 31 | 5.0 mg, 1.0 mm (W) | 3-times oxidized | 45° C. | 6.2 | 43.2 | 10 mg/ml DTE | V |
| 32 | 5.0 mg, 1.0 mm (W) | 3-times oxidized | 50° C. | 6.2 | 21.6 | 10 mg/ml DTE | V |
| 33 | 5.0 mg, 23.0 mm (W) | 3-times oxidized | 50° C. | 6.2 | 21.6 | 10 mg/ml DTE | V |
| 34 | 15 hairs (2.0 mg) 46.0 mm (W) | 3-times oxidized | 50° C. | 6.2 | 21.6 | 10 mg/ml DTE | V |
| 35 | 15 hairs (2.0 mg) 46.0 mm (W) | not oxidized | 50° C. | 6.2 | 21.6 | 10 mg/ml DTE | V |
| 36 | 100 hairs (14 mg) 46.0 mm (W) | 3-times oxidized | 50° C. | 6.2 | 21.6 | 10 mg/ml DTE | V |
| 37 | 100 hairs (14 mg) 46.0 mm (W) | not oxidized | 50° C. | 6.2 | 21.6 | 10 mg/ml DTE | V |
| 38 | 5.0 mg, 10.0 mm | 3-times oxidized | 50° C. | 6.2 | 21.6 | 10 mg/ml DTE | V |

-continued

| Example | Hair Sample (W) | Hair Treatment | Temp. | pH | Papain (U) | Reducing Agent | Remarks |
|---|---|---|---|---|---|---|---|
| 39 | 5.0 mg, 1.0 mm (W) | once oxidized | 50° C. | 6.2 | 21.6 | 10 mg/ml DTE | V |
| 40 | 5.0 mg, 1.0 mm (W) | twice oxidized | 50° C. | 6.2 | 21.6 | 10 mg/ml DTE | V |
| 41 | 5.0 mg, 1.0 mm (W) | 3-times oxidized | 50° C. | 6.2 | 10.8 | 10 mg/ml DTE | V |
| 42 | 5.0 mg, 1.0 mm | weathered, hair roots | 50° C. | 6.2 | 21.6 | 10 mg/ml DTE | V |
| 43 | 5.0 mg, 1.0 mm | weathered, hair tips | 50° C. | 6.2 | 21.6 | 10 mg/ml DTE | V |
| 44 | 5.0 mg, 1.0 mm (W) | 3-times oxidized | 50° C. | 7.0 | 21.6 | 20 mg/ml Cystein | V |
| 45 | 5.0 mg, 1.0 mm (W) | 3-times oxidized | 50° C. | 7.5 | 21.6 | 20 mg/ml Cystein | V |
| 46 | 5.0 mg, 1.0 mm (W) | 3-times oxidized | 50° C. | 6.5 | 21.6 | 20 mg/ml Cystein | V |
| 47 | 5.0 mg, 1.0 mm (W) | not oxidized | 50° C. | 6.5 | 21.6 | 20 mg/ml Cystein | V |
| 48 | 5.0 mg, 1.0 mm (W) | once oxidized | 50° C. | 6.5 | 21.6 | 20 mg/ml Cystein | V |
| 49 | 5.0 mg, 1.0 mm (W) | twice oxidized | 50° C. | 6.5 | 21.6 | 20 mg/ml Cystein | V |
| 50 | 5.0 mg, 1.0 mm (W) | 3-times oxidized | 50° C. | 6.5 | 21.6 | 20 mg/ml Cystein | V |
| 51 | 5.0 mg, 1.0 mm (W) | not oxidized | 50° C. | 5.5 | 21.6 | 20 mg/ml Cystein | V |
| 52 | 5.0 mg, 1.0 mm (W) | once oxidized | 50° C. | 5.5 | 21.6 | 20 mg/ml Cystein | V |
| 53 | 5.0 mg, 1.0 mm (W) | 3-times oxidized | 50° C. | 6.5 | 21.6 | 20 mg/ml Cystein | V |
| 54 | 5.0 mg, 1.0 mm (W) | not oxidized | 35° C. | 6.5 | 21.6 | 20 mg/ml Cystein | V |
| 55 | 5.0 mg, 1.0 mm (W) | once oxidized | 35° C. | 6.5 | 21.6 | 20 mg/ml Cystein | V |
| 56 | 5.0 mg, 1.0 mm (W) | 3-times oxidized | 35° C. | 6.5 | 21.6 | 20 mg/ml Cystein | V |
| 57 | 5.0 mg, 1.0 mm (W) | 3-times oxidized | 50° C. | 6.5 | 21.6 | 2.5 ml Phosphat pH 6.5; 0.5 ml 120 mg/ml Cystein | S[3] |
| 58 | 5.0 mg, 1.0 mm | once oxidized | 50° C. | 6.5 | 21.6 | 2.5 ml Phosphat pH 6.5; 0.5 ml 120 mg/ml Cystein | S |
| 59 | 5.0 mg, 1.0 mm | not oxidized | 50° C. | 6.5 | 21.6 | 2.5 ml Phosphat pH 6.5: 0.5 ml 120 mg/ml Cystein | S |
| 60 | 5.0 mg, 1.0 mm (W) | once oxidized | 40° C. | 6.5 | 21.6 | 20 mg/ml Cystein | V |
| 61 | 5.0 mg, 1.0 mm (W) | 3-times oxidized | 40° C. | 6.5 | 21.6 | 20 mg/ml Cystein | V |
| 62 | 5.0 mg, 1.0 mm (W) | once oxidized | 40° C. | 6.5 | 21.6 | 20 mg/ml Cystein + 20% EtOH | V |
| 63 | 5.0 mg, 1.0 mm (W) | 3-times oxidized | 40° C. | 6.5 | 21.6 | 20 mg/ml Cystein + 20% EtOH | V |
| 64 | 5.0 mg, 1.0 mm (W) | once oxidized | 40° C. | 6.5 | 21.6 | 20 mg/ml Cystein + 10% EtOH | V |

-continued

| Example | Hair Sample | Hair Treatment | Temp. | pH | Papain (U) | Reducing Agent | Remarks |
|---|---|---|---|---|---|---|---|
| 65 | 5.0 mg, 1.0 mm (W) | 3-times oxidized | 40° C. | 6.5 | 21.6 | 20 mg/ml Cystein + 10% EtOH | V |
| 66 | 5.0 mg, 1.0 mm (W) | once oxidized | 40° C. | 6.5 | 21.6 | 10 mg/ml Cystein + 20% EtOH | V |
| 67 | 5.0 mg, 1.0 mm (W) | 3-times oxidized | 40° C. | 6.5 | 21.6 | 10 mg/ml Cystein + 20% EtOH | V |
| 68 | 5.0 mg, 1.0 mm (W) | 3-times oxidized | 40° C. | 6.5 | 21.6 | 0.74 mg/ml Cystein 7.0 mg/ml $Na_2S_2O_5$ 3.0 mg/ml $Na_2SO_3$ | V |
| 69 | 5.0 mg, 1.0 mm (W) | 3-times oxidized | 40° C. | 6.5 | 21.6 | 10.74 mg/ml Cystein | V |
| 70 | 5.0 mg, 1.0 mm (W) | 3-times oxidized | 40° C. | 6.5 | 21.6 | 10 mg/ml Cystein 7.0 mg/ml $Na_2S_2O_5$ 3.0 mg/ml $Na_2SO_3$ | V |
| 71 | 5.0 mg, 1.0 mm (W) | not oxidized | 50° C. | 6.5 | 21.6 | 10 mg/ml DTE | V |
| 72 | 5.0 mg, 1.0 mm | weathered, hair tips | 50° C. | 6.5 | 21.6 | 10 mg/ml DTE | V |
| 73 | 5.0 mg, 1.0 mm | weathered, hair roots | 50° C. | 7.0 | 21.6 | 10 mg/ml DTE | V |
| 74 | 5.0 mg, 1.0 mm | weathered, hair roots | 50° C. | 6.5 | 21.6 | 10 mg/ml DTE | V |
| 75 | 5.0 mg, (W) 1.0 mm | 6 × DW | 50° C. | 6.5 | 21.6 | 20 mg/ml Cystein | V |
| 76 | 5.0 mg, (W) 1.0 mm | 3 × DW | 50° C. | 6.5 | 21.6 | 20 mg/ml Cystein | V |
| 77 | 5.0 mg, (W) 1.0 mm | 1 × DW | 50° C. | 6.5 | 21.6 | 20 mg/ml Cystein | V |

[1]V = 5-min preincubation, then papain;
[2]W = hair washed with 1% SDS as in Example 6;
[3]S = 5-min preincubation, then simultaneous addition of cysteine and papain;
[4]DW = permanent wave treatment as in Example 2.

What is claimed is:

1. A method for recognizing damage to a keratin-containing material and for determining an extent of the damage to the keratin-containing material, said method comprising the steps of:
  a) providing a liquid sample comprising an aqueous solution and the keratin-containing material;
  b) subjecting the keratin-containing material in the liquid sample to at least one of an enzymatic treatment for proteolytic or hydrolytic degradation of the keratin-containing material and a chemical treatment for proteolytic or hydrolytic degradation of the keratin-containing material; and
  c) evaluating and estimating turbidity in said liquid sample to determine the extent of the damage to the keratin-containing material.

2. The method as defined in claim 1, wherein said turbidity in said liquid sample is evaluated and estimated by visual observation with a naked eye of an observer.

3. The method as defined in claim 1, wherein the evaluating and estimating includes measuring said turbidity by a physical measuring method and wherein said physical measuring method is a light scattering method, a nephelometric method, a fluorescence method, a transmitted light intensity measurement method, an extinction coefficient measurement method or a turbidimetric measurement method.

4. The method as defined in claim 3, wherein said turbidity is measured with a photometer by a turbidity measurement method.

5. The method as defined in claim 1, wherein the keratin-containing material is subjected to the proteolytic or hydrolytic degradation by reacting the keratin-containing material with at least one enzyme selected from the group consisting of proteases which catalyze degradation of the keratin-containing material and proteinases which catalyze degradation of the keratin-containing material.

6. The method as defined in claim 5, wherein said at least one enzyme is selected from the group consisting of papain, pronase E, proteinase K, subtilisin, trypsin and keratinases.

7. The method as defined in claim 1, wherein the keratin-containing material is subjected to the proteolytic or hydrolytic degradation by reacting the keratin-containing material with at least one keratolytically active organic reagent, at least one reducing organic reagent, at least one keratolytically active inorganic reagent or at least one reducing inorganic reagent.

8. The method as defined in claim 1, wherein the keratin-containing material is subjected to the proteolytic or hydrolytic degradation by reacting the keratin-containing material with at least one compound and wherein said at least one compound is selected from the group consisting of urea, sodium hydroxide, tributylphosphine, sodium iodide, performic acid, ammonia, thioglycolic acid, acetic acid, cysteine, sodium metabisulfite, sodium sulfite, dithiothreitol and dithioerythrol.

9. The method as defined in claim 1, wherein the keratin-containing material is subjected to the proteolytic or hydrolytic degradation by reacting the keratin-containing material with a combination consisting of at least one enzyme and at least one keratolytically active organic reagent, at least one reducing organic reagent, at least one keratolytically active inorganic reagent or at least one reducing inorganic reagent.

10. The method as defined in claim 1, further comprising removing an undegraded portion of the keratin-containing material that has not been degraded by said at least one of said enzymatic treatment and said chemical treatment for the proteolytic or hydrolytic degradation prior to the evaluating and estimating of the turbidity so that the evaluating and estimating of the turbidity is performed in the absence of the undegraded portion.

11. The method as defined in claim 1, further comprising subjecting the liquid sample containing the keratin-containing material to mechanical stress during said at least one of the enzymatic treatment and chemical treatment for the proteolytic or the hydrolytic degradation.

12. The method as defined in claim 1, wherein the evaluating and estimating is not performed prior to the at least one of the enzymatic treatment and the chemical treatment.

13. The method as defined in claim 1, wherein the evaluating and estimating is carried out directly and discontinuously.

14. The method as defined in claim 1, wherein the evaluating and estimating is carried out directly and continuously.

15. The method as defined in claim 1, wherein the keratin-containing material is a skin appendage.

16. The method as defined in claim 15, wherein said skin appendage is hair, wool or fibers.

17. The method as defined in claim 3, wherein said method further comprises the steps of providing an apparatus for said measuring of said turbidity, said apparatus comprising a reaction vessel for containing the liquid sample, said liquid sample comprising the keratin-containing material, a photometer for measuring light intensities of light from the liquid sample contained in the reaction vessel, an adapter or support for holding the reaction vessel, a mixing device for mixing the liquid sample in the reaction vessel, said mixing device comprising a controllable drive for controlled stirring of the liquid sample, and a heating device for heating the liquid sample in the reaction vessel; placing the liquid sample in the reaction vessel; driving the mixing device at a predetermined mixing rate to mix the liquid sample placed in the reaction vessel; heating the liquid sample to a predetermined temperature and measuring the light intensities of the light from the liquid sample with the photometer.

18. The method as defined in claim 17, wherein the predetermined temperature of said liquid sample is measured with a thermocouple.

19. The method as defined in claim 17, wherein said heating device is a heating band.

20. The method as defined in claim 19, wherein the heating band is built into a wall of the adapter or the support for the reaction vessel.

21. The method as defined in claim 17, wherein said reaction vessel is a test tube or a cuvette.

22. The method as defined in claim 17, wherein the mixing device is a syringe with plunger or piston; a stirrer driven or moved by a mechanical, electrical or magnetic drive or an ultrasonic device.

23. The method as defined in claim 17, wherein at least one of the photometer, the heating device and the mixing device are connected electrically to at least one of a recorder, printer, video screen and computer.

24. The method as defined in claim 23, wherein said computer is a hand held portable processor device.

25. A kit of reagents for a method of detecting and determining an extent of damage to a keratin-containing material, said kit comprising a buffer solution and at least one member selected from the group consisting of keratinolytically active enzymes, proteolytically active chemical reagents, hydrolytically active reagents and reducing chemical reagents; and an apparatus for recognizing damage to the keratin-containing material and for determining an extent of the damage to the keratin-containing material;

wherein said apparatus comprises a reaction vessel for containing a liquid sample comprising the keratin-containing material; a photometer for measuring turbidity of the liquid sample in the reaction vessel; an adapter or support for holding the reaction vessel; a mixing device for mixing the liquid sample in the reaction vessel with a controllable drive for controlled mixing; and a heating device for heating the reaction vessel.

26. The kit as defined in claim 25, further comprising at least one of a portion of keratin-containing material and a liquid sample acting as a standard, blank or zero value preparation.

* * * * *